STRAWBERRY PLANT

Filed Nov. 14, 1973

United States Patent

Plant Pat. 3,715
Patented May 6, 1975

3,715
STRAWBERRY PLANT

Herschel L. Boll, R.R. 4, Champaign, Ill. 61820

Filed Nov. 14, 1973, Ser. No. 415,498
Int. Cl. A01h *5/03*
U.S. Cl. Plt.—49 1 Claim My invention relates to a new and distinct variety of strawberry plant. It is the result of a cross of [(Canall × Twentieth Century) × Twentieth Century] × Ogallala, made by me in 1967, at Champaign, Ill.

Since my discovery of the original plant, I have asexually reproduced a large number of plants from the original mother plant by rooted runners.

My object in the asexual propagation of the original mother plant was to determine the characteristics of the plant and of its fruit by the testing of a large number of plants. The distinguishing features of my new variety have proved to be permanent. My new variety has proved itself to have unusual possibilities because of its everbearing habit of growth, its high productivity, its vigorous growth, and its early season of maturity.

Figure 1:
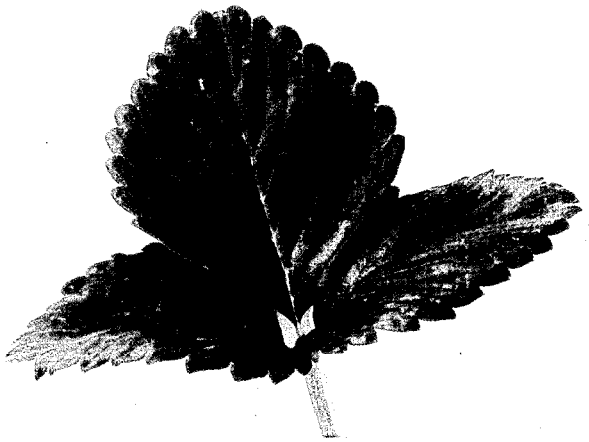
FIG. 1 shows a typical leaf in full color.
Figure 2:
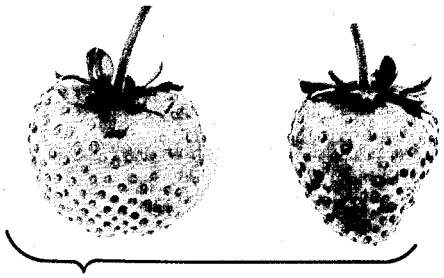
FIG. 2 illustrates two berries of typical shape.
Figure 3:
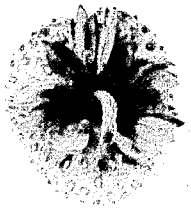
FIG. 3 shows a typical top view of a berry, exhibiting the large calyx.

In general, the distinct and new variety of strawberry plant, which is the subject of my invention and discovery, is characterized by its everbearing habit of growth, by its high productivity, by its vigorous growth (because of its plants that are medium in height, its many crowns per plant, its medium number of runners for an everbearer, its leaves that are medium in size and many in number, its wide leaflets, and its high productivity of large fruit), and by its early season of maturity. These characteristics I now refer to in greater detail. Color plate references are according to Color Standards and Color Nomenclature by Robert Ridgway.

Under the conditions at Champaign, Ill., my new variety of plant is everbearing and high in productivity (producing, the year after planting, about 1 to 1½ quarters of fruit per plant planted) largely because it bears two crops per year, the first crop being slightly larger than the second crop. It is adapted farther south in the Midwest than most other everbearers. It is even better adapted in southwestern Michigan. The plants are vigorous, and are medium in height. They produce a medium number of runners (about 3 to 4 per plant) for an everbearer, which is less than either Sonjana (Plant Pat. 1,691) or Gem.

The leaves are medium green in color, or are approximately Forest Green (Plate XVII), or varying from Varley's Green (Plate XVIII) to Forest Green (Plate XVII) to Cerro Green (Plate V), depending mainly on soil fertility, but also depending on other soil conditions, exposure, and weather and climatic conditions. The leaves are medium in size, slightly dull, relatively flat to slightly cupped, and relatively smooth. The leaflets are wide, the margins of which tend to curve downward. The terminal leaflet overlaps the lateral leaflets, and the lateral leaflets overlap at the base of the leaf. The flowers are perfect. The date of the first blossoms in 1973 at Champaign, Ill., was April 30.

At Champaign, Ill., my new variety of strawberry plant begins to mature its fruit early or at about the same time as Premier (Howard 17) and Sunrise, but the latter two varieties are June-bearers. The date of the first picking in 1973 at Champaign, Ill., was May 25. The harvesting period is about two weeks in length. The second crop is produced mostly in August. The berries are well formed throughout the bearing season.

The fruit is medium dark red (it is deep red for both Sonjana and Gem), or is approximately Carmine Red (Plate I), or varying from Nepal Red (Plate I) to Carmine Red (Plate I) to Ox-blood Red (Plate I), depending mainly on exposure, but also depending on soil, weather and climatic conditions. The fruit is large—larger in southwestern Michigan—up to 1¾ inches in diameter, and averaging about 1 to 1¼ inches. It is medium in size for Sonjana, and small to medium for Gem. The fruit of my new variety is wedge to conic in shape, while it is heart-shaped for Locke Lake Ruby (Plant Pat. 2,429), blunt conic for Sonjana, and short wedge to oblate for Gem. It is slightly glossy to glossy and slightly soft. Locke Lake Ruby is solid inside. The fruit stems are thick.

The calyx is large. Most sepals are 3-toothed instead of single-toothed. The achenes are about flush with the surface to slightly raised, and are yellow to red depending on exposure.

Under the conditions existing where I have reproduced and tested by new variety of strawberry plant, the flesh of the berry is medium red, but it is red with a whitish area for Locke Lake Ruby, and whitish for Sonjana. The fruit is subacid (it is acid for Gem), and is medium in flavor.

The strawberry above described, and the plant producing it, of course, may vary in slight details, depending on soil, weather, and climatic conditions.

What I claim is:

1. A new and distinct variety of strawberry plant substantially as herein shown and described, characterized by its everbearing habit of growth, by its high productivity, by its vigorous growth, and by its early season of maturity.

References Cited

UNITED STATES PATENTS

| | | | |
|---|---|---|---|
| P.P. 1,691 | 3/1958 | Hummel | Plants—49 |
| P.P. 2,429 | 7/1964 | Brunnen | Plants—49 |

ROBERT E. BAGWILL, Primary Examiner